(12) United States Patent
Malackowski

(10) Patent No.: US 9,339,346 B2
(45) Date of Patent: May 17, 2016

(54) SYSTEM AND METHOD FOR INTERACTING WITH AN OBJECT

(71) Applicant: Stryker Corporation, Kalamazoo, MI (US)

(72) Inventor: Donald W. Malackowski, Schoolcraft, MI (US)

(73) Assignee: STRYKER CORPORATION, Kalamazoo, MI (US)

( * ) Notice: Subject to any disclaimer, the term of this patent is extended or adjusted under 35 U.S.C. 154(b) by 13 days.

(21) Appl. No.: 14/505,801

(22) Filed: Oct. 3, 2014

(65) Prior Publication Data

US 2015/0100161 A1    Apr. 9, 2015

Related U.S. Application Data

(60) Provisional application No. 61/886,838, filed on Oct. 4, 2013.

(51) Int. Cl.
*A61B 19/00*    (2006.01)
*B25J 9/16*    (2006.01)

(52) U.S. Cl.
CPC ........... *A61B 19/2203* (2013.01); *B25J 9/1653* (2013.01); *A61B 2019/4894* (2013.01); *A61B 2019/5255* (2013.01); *A61B 2019/5259* (2013.01); *G05B 2219/45117* (2013.01)

(58) Field of Classification Search
CPC ................... A61B 19/2203; A61B 2019/5259; A61B 2019/5255; A61B 2019/4894; B25J 9/1653; G05B 19/45117
See application file for complete search history.

(56) References Cited

U.S. PATENT DOCUMENTS

| 7,725,162 | B2 | 5/2010 | Malackowski et al. |
| 2007/0270685 | A1 | 11/2007 | Kang et al. |
| 2008/0010706 | A1 | 1/2008 | Moses et al. |
| 2011/0118748 | A1 | 5/2011 | Itkowitz |
| 2013/0030286 | A1 | 1/2013 | Alouani et al. |

FOREIGN PATENT DOCUMENTS

WO    2013/052187 A2    4/2013

OTHER PUBLICATIONS

Dec. 18, 2014 International Search Report for PCT/US2014/059005.

*Primary Examiner* — James Trammell
*Assistant Examiner* — Adam Mott
(74) *Attorney, Agent, or Firm* — Howard & Howard Attorneys PLLC

(57) ABSTRACT

System and methods for positioning a tool in a robotic system include determining primary position information for the tool at a first frequency and determining secondary position information for the tool at a second frequency. The tool is moved in a first position control mode and a second position control mode based on the primary position information and the secondary position information. At least one of the first and second frequencies in each of the first and second position control modes is adjusted. A difference between the first and second frequencies in the first position control mode is different than a difference between the first and second frequencies in the second position control mode.

25 Claims, 7 Drawing Sheets

SYSTEM AND METHOD FOR INTERACTING WITH AN OBJECT

CROSS-REFERENCE TO RELATED APPLICATIONS

The subject patent application claims priority to and all the benefits of U.S. Provisional Patent Application No. 61/886,838 filed on Oct. 4, 2013, which is incorporated herein by reference.

TECHNICAL FIELD

The present invention relates generally to a system and method for interacting with an object, and more specifically, a system and method for controlling a tool that interacts with the object.

BACKGROUND

There is an emerging field for using systems, such as robotic systems, to assist medical personnel during a surgical procedure. These systems are configured so that a tool is maneuvered relative to an object of interest at a surgical site. The system typically includes a base with a plurality of linkages extending from the base. The system further includes a tool coupled to the plurality of linkages. The medical personnel may perform the surgical procedure with the system by providing instruction to the system to move the plurality of linkages and the tool with respect to the object.

Often a navigation system is employed to assist in accurately moving the tool to desired positions relative to the object. Navigation systems provide accurate position and orientation information for the tool and other objects being tracked, especially when these objects move within a relatively large working volume. The navigation-based position and orientation information is often provided to at least partially influence movement and positioning of the linkages of the system relative to a patient's anatomy of interest.

Additionally, movement of the tool can be controlled in an open loop fashion using position and orientation information derived from a plurality of encoders associated with the plurality of linkages. When utilized for relatively small movements, such encoders can provide more precision than the navigation system in a localized area of interest. As such, encoder-based position and orientation information may be useful when there is a desire to operate at a faster rate outside of the closed loop control of the navigation system. Thus, there are different benefits to using the navigation system and/or the encoders for generating movement commands.

Conventional systems face challenges with managing the navigation-based and encoder-based information. Mainly, the linkages exhibit a response frequency that is slower than the frequency at which the navigation-based position and orientation information is provided. More specifically, the linkages, motors, joints, etc. of most systems have some flexibility or play. This flexibility limits the reaction time between movement commands and ultimate movement and settling of the tool. If the position and orientation information from the navigation system is utilized for generating movement commands at a frequency faster than the tool is able to move and settle in reaction to such movement commands, the closed loop control of the system will become unstable. Additionally, the slow response frequency of the linkages inhibits the frequency at which this navigation-based position and orientation information can be utilized to influence positioning of the tool. Moreover, conventional systems do not allow for dynamic adjustment of the aforementioned frequencies. Thus, the versatility and stability of conventional systems is limited for various applications and situations.

Accordingly, there is a need in the art for systems and methods for solving the aforementioned problems.

SUMMARY

A system is provided for interacting with an object. The system comprises a robotic manipulator having a base and a plurality of linkages. A tool is coupled to the robotic manipulator and movable relative to the base to interact with the object. A plurality of position sensors are associated with the plurality of linkages for providing primary position information at a first frequency. A localizer provides secondary position information at a second frequency. A position controller is configured to position the tool with respect to the object in a first position control mode and a second position control mode based on the primary position information and the secondary position information. A frequency controller is configured to adjust at least one of the first and second frequencies in each of the first and second position control modes. A difference between the first and second frequencies in the first position control mode is different than a difference between the first and second frequencies in the second position control mode.

A method for positioning a tool in a robotic system is provided. The method includes determining primary position information for the tool at a first frequency. Secondary position information for the tool is determined at a second frequency. The tool is moved in a first position control mode and a second position control mode based on the primary position information and the secondary position information. At least one of the first and second frequencies in each of the first and second position control modes is adjusted. A difference between the first and second frequencies in the first position control mode is different than a difference between the first and second frequencies in the second position control mode.

The system and method effectively provide for customized control of the tool. The difference between the first and second frequencies affects the positional accuracy and positional speed of the tool. Thus, adjusting the difference between the first and second frequencies allows control over the positional speed and the positional accuracy of the tool.

Additionally, the difference between the first and second frequencies is different between the first and second position control modes. As such, the first and second position control modes have different parameters for the positional accuracy and positional speed of the tool. The system and method can operate according to the first or second position control modes depending on the desired positional accuracy and speed appropriate for the application and situation.

The system and method additionally provide stability because the first and second frequencies can be dynamically adjusted. If the difference between the first and second frequencies is causing instability, the difference can be dynamically adjusted.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
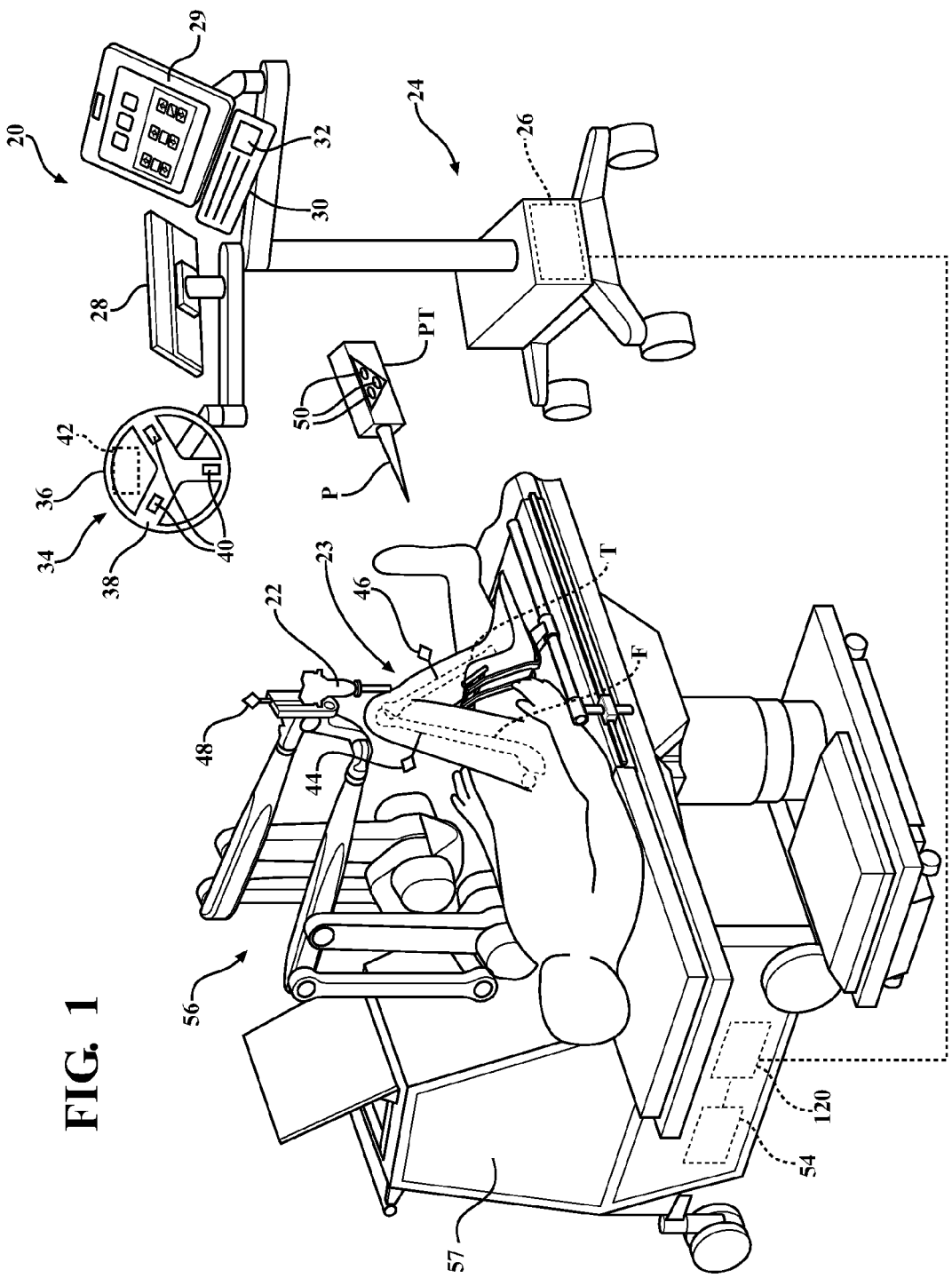
FIG. 1 is a perspective view of a guidance station being used in conjunction with a robotic manipulator.

Systems and methods are disclosed for positioning a tool 22 of a robotic system. The tool 22 is coupled to a robotic manipulator 56 and moves relative to a predefined path or anatomical boundary. The tool 22 is positioned with respect to an object or objects 23. Examples of the object 23, include, but are not limited to, anatomical features of a patient. In FIG. 1, the anatomy of the patient shown includes a femur F and a tibia T. The tool 22 interacts with the objects 23, and in some instances, manipulates the objects 23.

Figure 2:
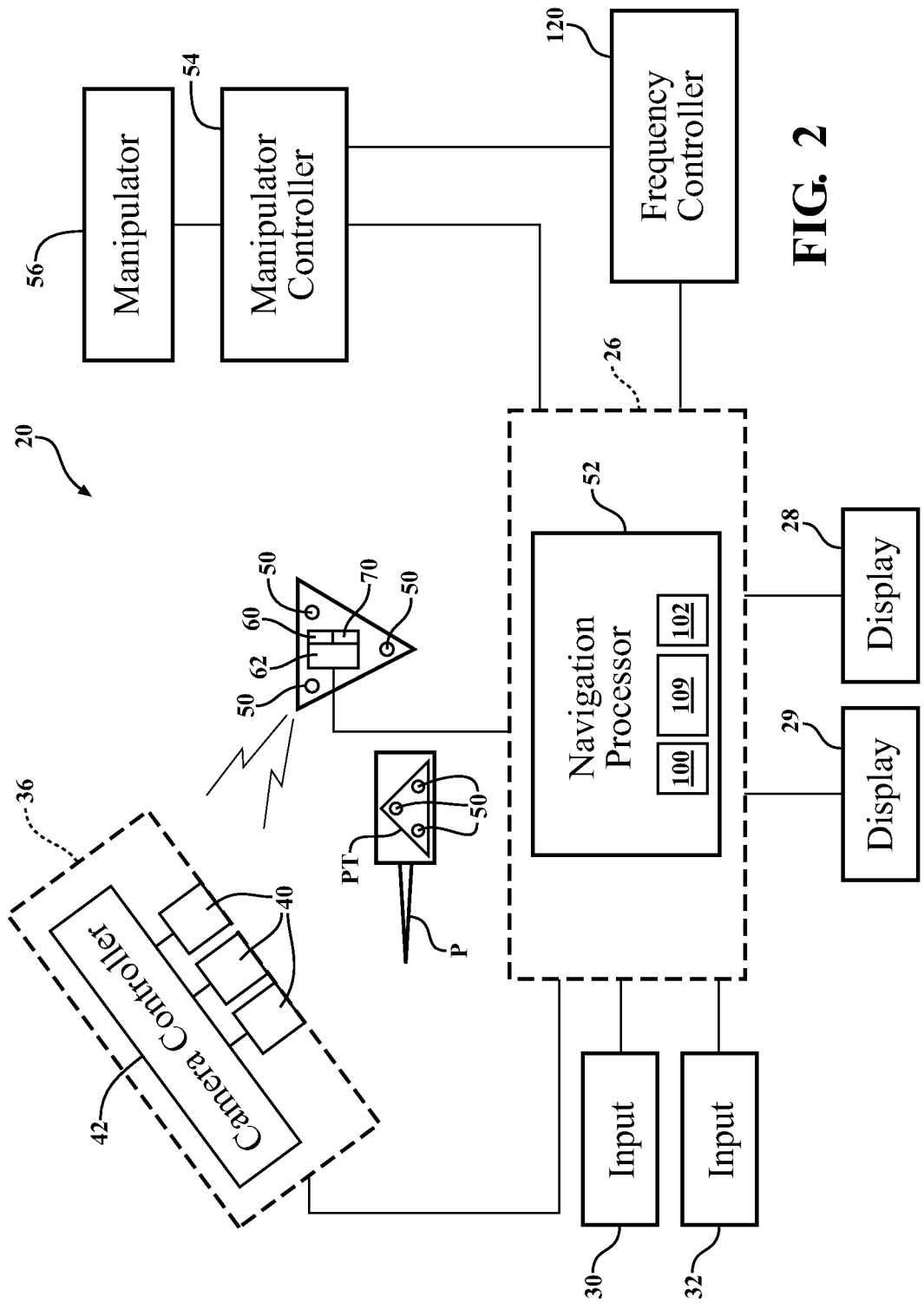
FIG. 2 is a schematic view of the guidance station, tracking devices, pointer, and robotic manipulator.

Referring to FIGS. 1 and 2, in one embodiment, the system includes a guidance station 20 coupled to the robotic manipulator 56. In FIG. 1, the guidance station 20 is shown in an operating room of a medical facility. The guidance station 20 is set up to track movement of various items in the operating room. Such items may include the anatomy of the patient and the tool 22. The guidance station 20 tracks these items for purposes of displaying their relative positions and orientations to the medical personnel. In some cases, the guidance station 20 tracks these items for purposes of controlling or constraining movement of the tool 22 relative to a predefined path or anatomical boundary.

The guidance station 20 includes a computer cart assembly 24 that houses a navigation computer 26, or other type of control unit. A navigation interface is in operative communication with the navigation computer 26. In one embodiment, the navigation interface includes a first display 28 adapted to be situated outside of the sterile field and a second display 29 adapted to be situated inside the sterile field. The displays 28, 29 are adjustably mounted to the computer cart assembly 24. First and second input devices 30, 32 such as a keyboard and mouse can be used to input information into the navigation computer 26 or otherwise select/control certain aspects of the navigation computer 26. Other input devices are contemplated including a touch screen (not shown) or voice-activation.

A localizer 34 communicates with the navigation computer 26. In the embodiment shown, the localizer 34 is an optical localizer and includes a camera unit 36 (also referred to as a sensing device). The camera unit 36 has an outer casing 38 that houses one or more optical position sensors 40. In some embodiments, at least two optical sensors 40 are employed, preferably three or more. The optical sensors 40 may be three separate charge-coupled devices (CCD). In one embodiment, three one-dimensional CCDs are employed. In other embodiments, separate camera units, each with a separate CCD, or two or more CCDs, may also be arranged around the operating room. The CCDs detect infrared (IR) signals. The localizer 34 may have any suitable configuration for communicating with the navigation computer 26.

Camera unit 36 is mounted on an adjustable arm to position the optical sensors 40 with a field of view of the below discussed trackers that, ideally, is free from obstructions. The adjustable arm allows adjustment of the camera unit 36 in at least one degree of freedom and, in some embodiments, in two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). Position and orientation signals and/or data are transmitted from the camera unit 36 to the navigation computer 26 for purposes of tracking the items.

The displays 28, 29 and camera unit 36 may be like those described in U.S. Pat. No. 7,725,162 to Malackowski, et al., issued on May 25, 2010, entitled "Surgery System," which is hereby incorporated by reference.

The navigation computer 26 can be a personal computer or laptop computer. Navigation computer 26 has the displays 28, 29, central processing unit (CPU) and/or other processors, memory (not shown), and storage (not shown). The navigation computer 26 is loaded with software as described below. The software converts the signals/data received from the camera unit 36 into data representative of the position and orientation of the items being tracked.

Guidance station 20 communicates with a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. In one embodiment, the trackers 44, 46 may be attached to the femur F and tibia T in the manner shown in U.S. Pat. No. 7,725,162, which is hereby incorporated by reference. Trackers 44, 46 could also be mounted like those shown in U.S. Provisional Patent Application No. 61/753,219, filed on Jan. 16, 2013, entitled, "Tracking Devices and Navigation Systems and Methods for Use Thereof," which is hereby incorporated by reference. In additional embodiments, a tracker is attached to the patella (not shown) to track a position and orientation of the patella. In yet further embodiments, the trackers 44, 46 could be mounted to other tissue types or parts of the anatomy.

A tool tracker 48 is rigidly attached to the tool 22. The tool tracker 48 may be integrated into the tool 22 during manufacture or may be separately mounted to the tool 22 in preparation for the surgical procedure. The working end of the tool 22, which is being tracked by virtue of the tool tracker 48, may be a rotating bur, electrical ablation device, or the like. The working end of the tool 22 may be presented by a separate energy applicator such as the rotating bur, electrical ablation device, etc. that forms part of the tool 22.

The trackers 44, 46, 48 may be battery powered with an internal battery or have leads to receive power through the navigation computer 26, which, like the camera unit 36, receives external power.

In the embodiment shown, the tool 22 forms part of an end effector on the robotic manipulator 56. The robotic manipulator 56 has a base 57, a plurality of linkages extending from the base 57, and a plurality of active joints for moving the tool 22 with respect to the base 57. The robotic manipulator 56 has the ability to operate in a manual mode, an autonomous mode, or a semi-autonomous mode. Such an arrangement is shown in U.S. Provisional Patent Application No. 61/679,258, entitled, "Surgical Manipulator Capable of Controlling a Surgical Tool in either a Semi-Autonomous Mode or a Manual, Boundary Constrained Mode," the disclosure of which is hereby incorporated by reference. A separate tracker (not shown) may be attached to the base 57 of the robotic manipulator 56 to track movement of the base 57.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 transmitting light, such as infrared light. The optical sensors 40 preferably have sampling rates of at least 100 Hz, more preferably at least 300 Hz, and most preferably at least 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, 48.

Referring to FIG. 2, each of the LEDs 50 are connected to a tracker controller 62 located in a housing (not shown) of the associated tracker 44, 46, 48 that transmits/receives data to/from the navigation computer 26. In one embodiment, the tracker controllers 62 transmit data on the order of several Megabytes/second through wired connections with the navigation computer 26. In other embodiments, a wireless connection may be used. In these wireless embodiments, the navigation computer 26 has a transceiver (not shown) to receive the data from the tracker controller 62.

In other embodiments, the trackers 44, 46, 48 may have passive markers (not shown), such as reflectors that reflect light emitted from the camera unit 36. The reflected light is then received by the optical sensors 40. Active and passive tracking elements are well known in the art.

The navigation computer 26 includes a navigation processor 52. The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical signals, navigation processor 52 generates data indicating the relative positions and orientations of the trackers 44, 46, 48 relative to the localizer 34. In some embodiments, the trackers 44, 46, 48 also include a gyroscope sensor 60 and accelerometer 70, such as the trackers shown in U.S. Provisional Patent Application No. 61/753,219, filed on Jan. 16, 2013, entitled, "Tracking Devices and Navigation Systems and Methods for Use Thereof," which is hereby incorporated by reference.

It should be understood that the navigation processor 52 may include one or more processors to control operation of the navigation computer 26. The processors may be any type of microprocessor or multi-processor system. The term processor is not intended to limit any scope to a single processor.

Based on the positions of the LEDs 50 and previously loaded data relating to the patient's anatomy and geometric information associated with the tool 22, navigation processor 52 determines the position and orientation of the tool 22 relative to the tissue (e.g., femur F and tibia T) against which the working end is to be applied. The previously loaded data includes data associated with pre-operative images, including for example, MRI images and CT scans, taken before the surgical procedure. The previously loaded data also includes geometric relationships between the working end of the tool 22 and the LEDs 50 on tool tracker 48.

Using well known navigation techniques for registration and coordinate system transformation, the patient's anatomy and the working end of the tool 22 can be registered into a coordinate reference frame of the localizer 34 so that the working end and the anatomy can be tracked together using the LEDs 50. A transformation matrix is provided to transform the coordinates of the tool 22 and the patient's anatomy from the localizer coordinate system LCLZ into a manipulator coordinate system MNPL as described below.

A manipulator controller 54 can use the position and orientation data of the tool 22 and the patient's anatomy to control the robotic manipulator 56 as described in U.S. Provisional Patent Application No. 61/679,258, entitled, "Surgical Manipulator Capable of Controlling a Tool in either a Semi-Autonomous Mode or a Manual, Boundary Constrained Mode," the disclosure of which is hereby incorporated by reference. Position and orientation data and other data may be transmitted by the navigation computer 26 to the manipulator controller 54 across wired or wireless connections.

The navigation processor 52 or manipulator controller 54 also generates image signals that indicate the relative position of the tool working end to the surgical site. These image signals are applied to the displays 28, 29. Displays 28, 29 generate images based on these signals that allow the surgeon and surgical personnel to view the relative position of the tool working end to the surgical site. The displays, 28, 29, as discussed above, may include a touch screen or other input/output device that allows entry of commands.

Figure 4:
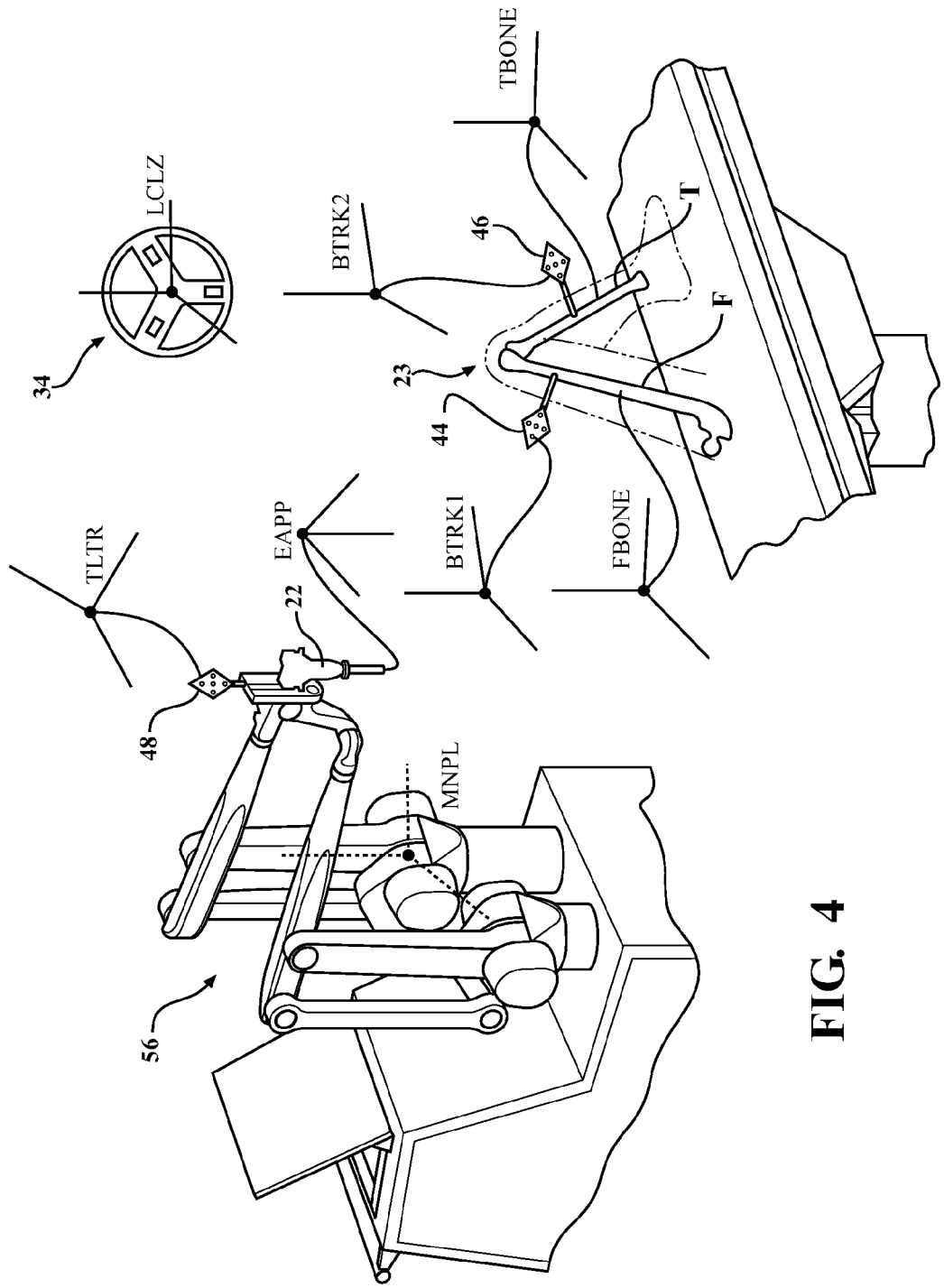
FIG. 4 is a schematic view of coordinate systems for the localizer and manipulator and other objects.

Referring to FIG. 2, a localization engine 100 is a software module that can be considered part of the guidance station 20 (or manipulator controller 54 in some embodiments). Localization engine 100 receives signals from the camera controller 42 and, in some embodiments, non-optically based signals from the tracker controller 62. Based on these signals, localization engine 100 determines the pose of the trackers 44, 46, 48 in the localizer coordinate system LCLZ. The localization engine 100 forwards the signals representative of the poses of trackers 44, 46, 48 to a coordinate transformer 102. Coordinate transformer 102 is another software module that forms part of the guidance station 20 (or manipulator controller 54 in some embodiments). Coordinate transformer 102 references the data that defines the relationship between the pre-operative images of the patient and the patient trackers 44, 46. Coordinate transformer 102 also stores the data indicating the pose of the working end of the tool 22 relative to the tool tracker 48. The various coordinate systems of the tool 22, the trackers 44, 46, 48, and the object 23 are shown in FIG. 4.

The coordinate transformer 102 then generates data indicating the position and orientation of the working end of the tool 22 relative to the tissue (e.g., bone) against which the working end is applied. The coordinate transformer 102 also operates to transform the data indicating the pose of the working end of the tool 22 relative to the tissue into the manipulator coordinate system MNPL described further below. Image signals representative of these data are forwarded to displays 28, 29 enabling the surgeon and surgical personnel to view this information. To avoid interruption of this data, the line-of-sight between the trackers 44, 46, 48 and the sensors 40 is to be maintained. If there are obstructions to the line-of-sight, then errors may occur.

Figure 3:
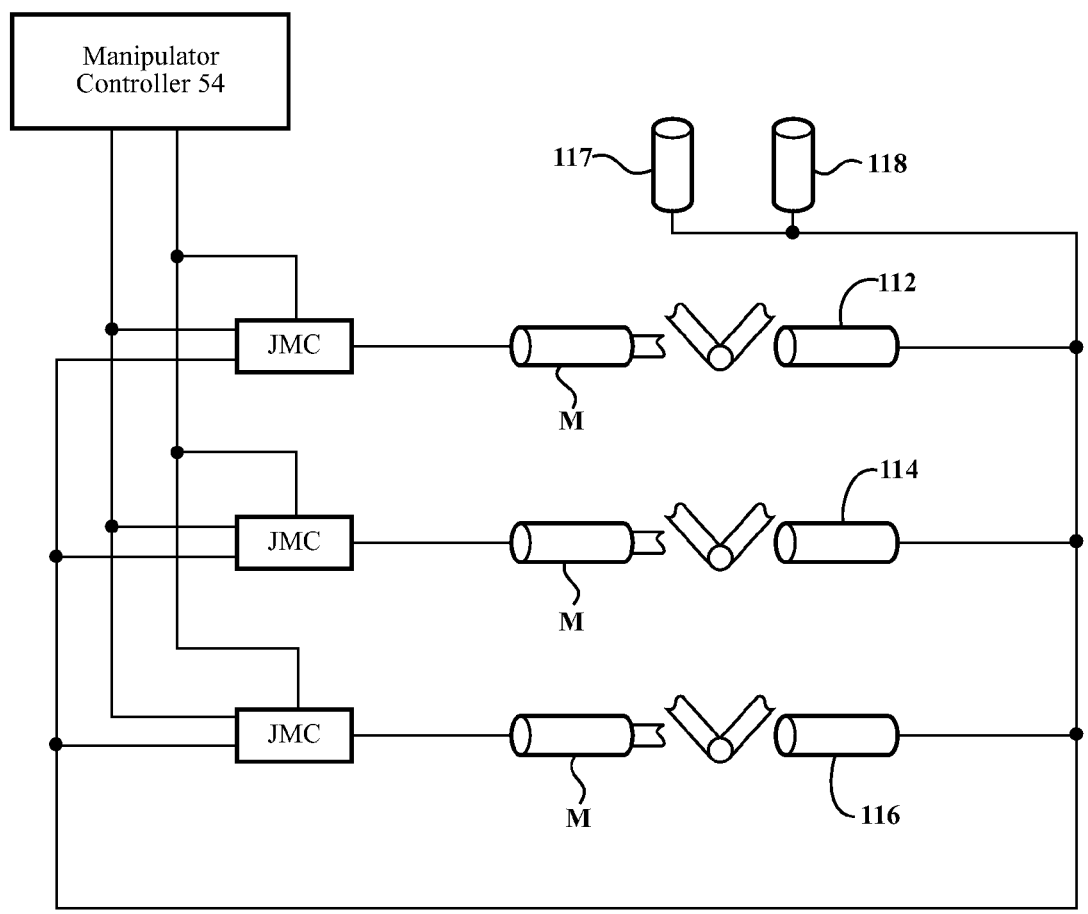
FIG. 3 is a schematic view of encoders and joint motor controllers of the robotic manipulator.

Referring to FIG. 3, a plurality of position sensors are associated with the plurality of linkages of the robotic manipulator 56. In one embodiment, the position sensors are encoders 112, 114, 116. The encoders 112, 114, 116 may be any suitable type of encoder, such as rotary encoders. As shown in FIG. 3, each encoder 112, 114, 116 is associated with an actuator, such as motor M. Each encoder 112, 114, 116 is a sensor that monitors the angular position of one of three motor driven components of the robotic manipulator 56 with which the encoder is associated. Robotic manipulator 56 includes two additional encoders, encoder 117 and 118.

Encoders 117 and 118 are associated with additional driven linkages. In some embodiments, the robotic manipulator 56 includes two arm structures with six encoders at six active joints.

Manipulator controller 54 determines the desired location to which the tool 22 should be moved, as described in U.S. Provisional Patent Application No. 61/679,258, entitled, "Surgical Manipulator Capable of Controlling a Tool in either a Semi-Autonomous Mode or a Manual, Boundary Constrained Mode," the disclosure of which is hereby incorporated by reference. Based on this determination, and information relating to the current location (e.g., pose) of the tool 22, the manipulator controller 54 determines the extent to which each linkage needs to be moved in order to reposition the tool 22 from the current location to the desired location. The data regarding where the linkages are to be positioned is forwarded to joint motor controllers JMC that control active joints of the robotic manipulator 56 to move the linkages and thereby move the tool 22 from the current location to the desired location.

In order to determine the current location of the tool 22, data from the encoders 112, 114, 116, 117 and 118 is used to determine measured joint angles. The measured joint angles of the active joints are forwarded to a forward kinematics module (not shown). Also applied to the forward kinematics module are the signals from encoders 117 and 118. These signals are the measured joint angles for the passive joints integral with these encoders. Based on the measured joint angles and preloaded data, the forward kinematics module determines the pose of the tool 22 in the manipulator coordinate system MNPL. The preloaded data are data that define the geometry of the linkages and joints.

In one embodiment, the manipulator controller 54 and joint motor controllers JMC collectively form a position controller that operates to move the tool 22 to commanded positions and/or orientations. The position controller operates in a position control loop. The position control loop may include multiple position control loops in parallel or series for each active joint. The position control loop processes position and orientation information to indicate and direct the pose of the tool 22.

As is described in detail below, the position sensors provide primary position information. In one example, the primary position information includes a pose of the tool 22 calculated based on information from the encoders 112, 114, 116, 117 and 118 and the preloaded data. Data from the encoders 112, 114, 116, 117, and 118 and preloaded data can be used to calculate the primary position information, in step 204. Additionally or alternatively, the primary position information includes a position and orientation of the tool 22 in the manipulator coordinate system MNPL. Alternatively, the primary position information includes position commands for commanding movement of the tool 22 in the manipulator coordinate system MNPL.

The navigation system provides secondary position information. More specifically, the localizer 34 provides secondary position information. In one example, the secondary position information includes a navigation-based pose of the tool 22 calculated in the localizer coordinate system LCLZ in step 200. In another example, the secondary position information includes position and orientation data transformed from the localizer coordinate system LCLZ to the manipulator coordinate system MNPL. The secondary position information may be processed by the navigation computer 26.

Referring to FIG. 4, relative positions of the localizer coordinate system LCLZ and the manipulator coordinate system MNPL are established so that a transformation matrix can be generated by the navigation computer 26. The transformation matrix transforms position and orientation data for items from the localizer coordinate system LCLZ to the manipulator coordinate system MNPL. This step may occur before the surgical procedure begins, and periodically during the surgical procedure as described further below. Additionally, primary position information may be generated after the transformation matrix is initially generated.

Figure 5:
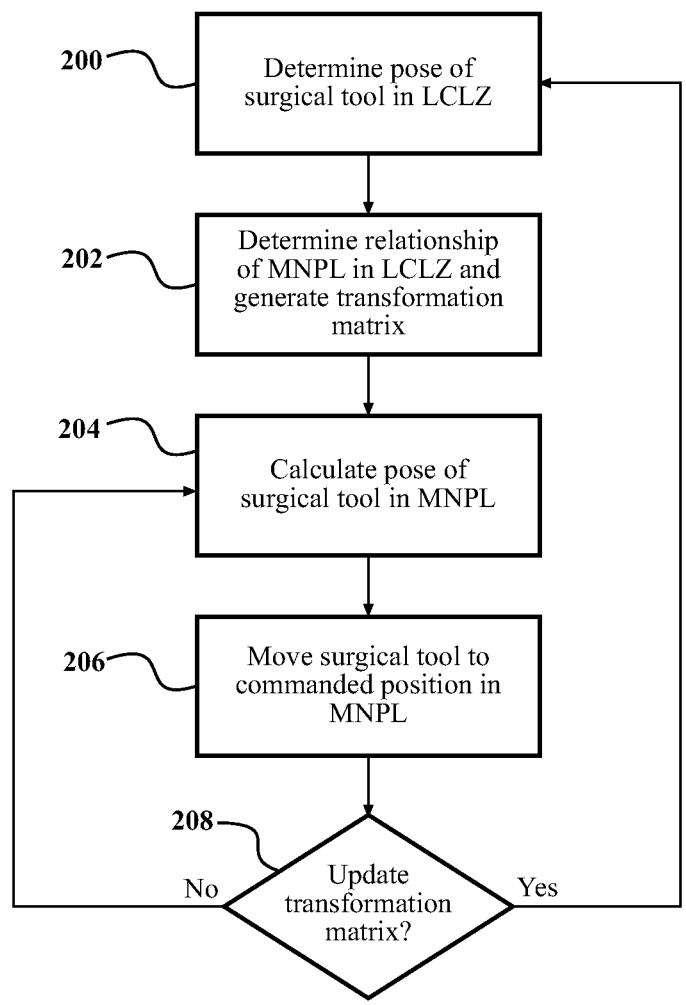
FIG. 5 is a flow chart of steps taken in one method.

Referring to FIG. 5, position and orientation of the tool tracker 48 is determined in the localizer coordinate system LCLZ so that the secondary position information can be calculated in the localized coordinate system LCLZ. The navigation-based pose of the tool 22 in the localizer coordinate system LCLZ is set as the pose from which the relative pose of the manipulator coordinate system MNPL can be kinematically determined.

The pose of the manipulator coordinate system MNPL relative to the localizer coordinate system LCLZ is based on data from the encoders 112, 114, 116, 117 and 118 and preloaded data. The preloaded data is associated with the relationship of the manipulator coordinate system MNPL to the encoders 112, 114, 116, 117 and 118, linkages, etc. As a result, the transformation matrix between the two coordinate systems can be generated in step 202. The tool 22 is moved by the position controller so that the tool 22, and in turn, the working end of the tool 22, is moved to the next commanded position in step 206.

Periodic adjustments are made using newly acquired navigation-based pose data of the tool 22 to update the transformation matrix. Updating the transformation matrix resets the manipulator coordinate system MNPL relative to the localizer coordinate system LCLZ. One reason for these periodic adjustments is that the encoder-based data is unable to account for any bending of the linkages of the robotic manipulator 56. Instead, such bending is accounted for by estimating forces on the arms. As a result, the navigation-based data complements the encoder-based data since any errors associated with bending of the linkages is automatically accounted for when measuring pose, for instance, with the localizer 34 and tool tracker 48.

The navigation computer 26 periodically updates the transformation matrix to reset the manipulator coordinate system MNPL. This is done to adjust for position inaccuracy that could result from positioning the tool 22 in an open-loop fashion based solely on encoder-derived pose data. By doing so, the encoder-based position and orientation of the tool 22 is corrected/re-calibrated using the navigation-based position and orientation information provided by the navigation computer 26 (i.e., by closing the control loop).

The primary position information is determined at a first frequency. In one embodiment, the position sensors determine the primary position information at the first frequency. Additionally or alternatively, the position controller may determine the primary position information at the first frequency. More specifically, using the signals from the position sensors, the position controller may generate position commands at the first frequency. As such, the first frequency may be defined as a position command frequency in some instances. In such instances, such as those described herein, the term "position command frequency" may be used instead of "first frequency."

Additionally, the secondary position information is determined at a second frequency. Specifically, the secondary position information is determined by updating the transformation matrix at the second frequency. Said differently, transformation of the position and orientation data is updated from the localizer coordinate system LCLZ to the manipulator coordinate system MNPL at the second frequency. As such, the second frequency may be defined as a transformation update frequency in some instances. In such instances, such as those described herein, the term "transformation update frequency" may be used instead of "second frequency." The transformation update frequency may be established by the manipulator controller 54. Additionally or alternatively, the transformation update frequency may be established by the navigation computer 26 and/or localizer 34.

In step 208, a determination is made whether the transformation matrix is to be updated based on the transformation update frequency. If the transformation matrix is not yet to be updated, as dictated by the transformation update frequency, then the method continues to step 204. If the transformation matrix is to be updated, then the method continues back to step 200.

The position controller is configured to position the tool 22 with respect to the object 23 in a first position control mode and a second position control mode. The position controller positions the tool 22 in the first and second position control modes based on the primary position information and the secondary position information.

As shown in FIGS. 1 and 2, the system includes a frequency controller 120. The frequency controller is configured to adjust at least one of the first and second frequencies. Adjustment of the first and second frequencies is made in the first position control mode and the second position control mode.

In one embodiment, the frequency controller 120 is coupled to both the manipulator controller 54 and the navigation computer 26. The frequency controller 120 may be disposed in any suitable location. For example, as shown in FIG. 1, the frequency controller 120 is disposed in the robotic manipulator 56. Alternatively, the frequency controller 120 may be disposed in the guidance station 20. The frequency controller 120 may be a standalone component or integrated as a sub-component of larger device, such as the manipulator controller 54 or the navigation computer 26.

The frequency controller 120 adjusts the first and second frequencies so that a difference between the first and second frequencies in the first position control mode is different than a difference between the first and second frequencies in the second position control mode. In one embodiment, the difference between the first and second frequencies is a mathematical subtraction of the second frequency from the first frequency. For example, if the first frequency is 1 KHz and the second frequency is 900 Hz, the difference is 100 Hz. Alternatively, the difference between the first and second frequencies is a mathematical subtraction of the first frequency from the second frequency. The difference may be an absolute difference whereby the absolute value of difference between the first and second frequency is determined. Those skilled in the art appreciate that the difference between the first and second frequencies may be derived according to various other mathematical operations, including, but not limited to, addition, division, differentiation, integration, and the like.

The difference may be discretely measured for any given moment during operation in any given position control mode. For example, the difference between the first and second frequencies in the first position control mode is measured instantaneously at a given time. The difference in the first position control mode measured instantaneously at the given time may be discretely different than the difference in the second position control mode measured instantaneously at the same given time. Alternatively, the difference may be continuously measured during operation in any given position control mode. In such instances, the difference in the first position control mode may be continuously different than the difference in second position control mode. In one example, the difference is averaged over a period of time. Here, the average difference between the first and second frequencies in the first position control mode is different than the average difference between the first and second frequencies in the second position control mode.

The difference between the first and second frequencies influences a positional speed of the tool 22 and a positional precision or accuracy of the tool 22. The positional speed is also known as the feed-rate at which the tool 22 moves.

In one sense, the difference between the first and second frequencies signifies the extent to which the primary and secondary position information is used in moving the tool 22. As described, when the tool 22 is being positioned in a relatively large area of interest, the positional accuracy of the tool 22 is greater when derived from navigation-based secondary position information rather than when derived from encoder-based primary position information.

As a trade-off to the high degree of positional accuracy, the positional speed of the tool 22 is slower when derived from the secondary position information as compared with when derived from the primary position information. In other words, the positional speed of the tool 22 is faster when derived from the primary position information as compared with the secondary position information.

Generally, the positional speed increases as the difference between the first and second frequencies increases. Conversely, the positional speed decreases as the difference between the first and second frequencies decreases.

Additionally, the positional accuracy increases as the difference between the first and second frequencies decreases. For example, in some cases, such as when the tool 22 is being positioned in a relatively large area of interest, the closer the transformation update frequency is to the position command frequency, the more accurate the positioning of the tool 22. On the other hand, the positional accuracy decreases as the difference between the first and second frequencies increases.

In one embodiment, the difference between the first and second frequencies in the first position control mode is greater than the difference between the first and second frequencies in the second position control mode. In some instances, the difference between the first and second frequencies in both the first position control mode and the second position control mode is non-zero. Here, the non-zero difference between the first and second frequencies in the first position control mode is greater than the non-zero difference between the first and second frequencies in the second position control mode.

In another embodiment, the difference between the first and second frequencies in the first position control mode is non-zero. The first frequency is greater than the second frequency in the first position control mode. The transformation matrix is periodically updated at a transformation update frequency less than the frequency with which position commands are generated by the position controller. Meanwhile, the difference between the first and second frequencies in the second position control mode is approximately zero. This difference is less than the non-zero difference in the first position control mode. The first frequency is substantially equal to the second frequency in the second position control mode. Said differently, the transformation matrix is periodically updated at a transformation update frequency substantially equal to the frequency with which position commands are generated by the position controller.

Accordingly, in this embodiment, the positional speed of the tool 22 in the first position control mode is greater than the positional speed of the tool 22 in the second position control mode. In the second position control mode, the positional accuracy of the tool 22 is greater than the positional accuracy of the tool 22 in the first position control mode. As such, the first position control mode is preferred over the second position control mode if bulk cutting in a larger area of interest is desired. However, the second position control mode is preferred over the first position control mode if precision cutting is desired.

For this embodiment, positioning of the tool 22 in the first position control mode is primarily controlled in an open-loop fashion by the position controller using the encoder-based pose information in the manipulator coordinate system MNPL. In this first position control mode, position commands are sent to the joint motor controllers JMC at a relatively high command frequency, i.e., a frequency greater than a response frequency associated with the plurality of linkages and the tool 22. The response frequency of the plurality of linkages and the tool 22 is the frequency at which complete movement and settling of the tool 22 occurs in response to a position command. Since the linkages, motors, joints, etc. of the robotic manipulator 56 have some flexibility or play there is a limitation on the reaction time between position commands and complete movement and settling of the tool 22.

As such, in this embodiment, the transformation update frequency in the first position control mode is adjusted to be less than the position command frequency and less than the response frequency of the linkages and the tool 22. If the transformation update frequency was instead set faster than the response frequency, the system may become unstable. As a result, since position commands are being generated at a higher frequency than the transformation update frequency, there is potentially lower accuracy in positioning the tool 22 at the surgical site.

The difference between the first and second frequencies in the first position control mode may be of varying degree. In some cases, the transformation update frequency in the first position control mode is 1/10 or less than the command frequency with which position commands are sent to the joint motor controllers JMC.

In the second position control mode, the transformation update frequency may be at approximately the same command frequency with which position commands are sent to the joint motor controllers JMC. As such, in some situations like those in which the tool 22 is being positioned in a relatively large area of interest, the system can more accurately place the tool 22 at the surgical site than in the first position control mode. When switching to the second position control mode, the system will "slow down." In other words, the navigation computer 26 and the position control loop will work together to track and position the tool 22, but at a frequency less than the response frequency associated with the plurality of linkages and movement and settling of the tool 22. Again, this is done in order to avoid instability. Thus, in some embodiments, the transformation update frequency may be fixed based on the response frequency of the linkages and the command frequency is adjusted relative to the transformation update frequency to adjust accuracy.

The difference between the first and second frequencies in the second position control mode may be of varying degree. In some embodiments, the transformation update frequency in the second position control mode is greater than 1/10 of the command frequency in which position commands are sent to the joint motor controllers JMC.

Additionally, the system may include a plurality of position control modes in addition to the first and second position control modes. For example, the system may include blended modes having frequency and/or positional accuracy and speed parameters different than the first and second control modes.

Figure 6:
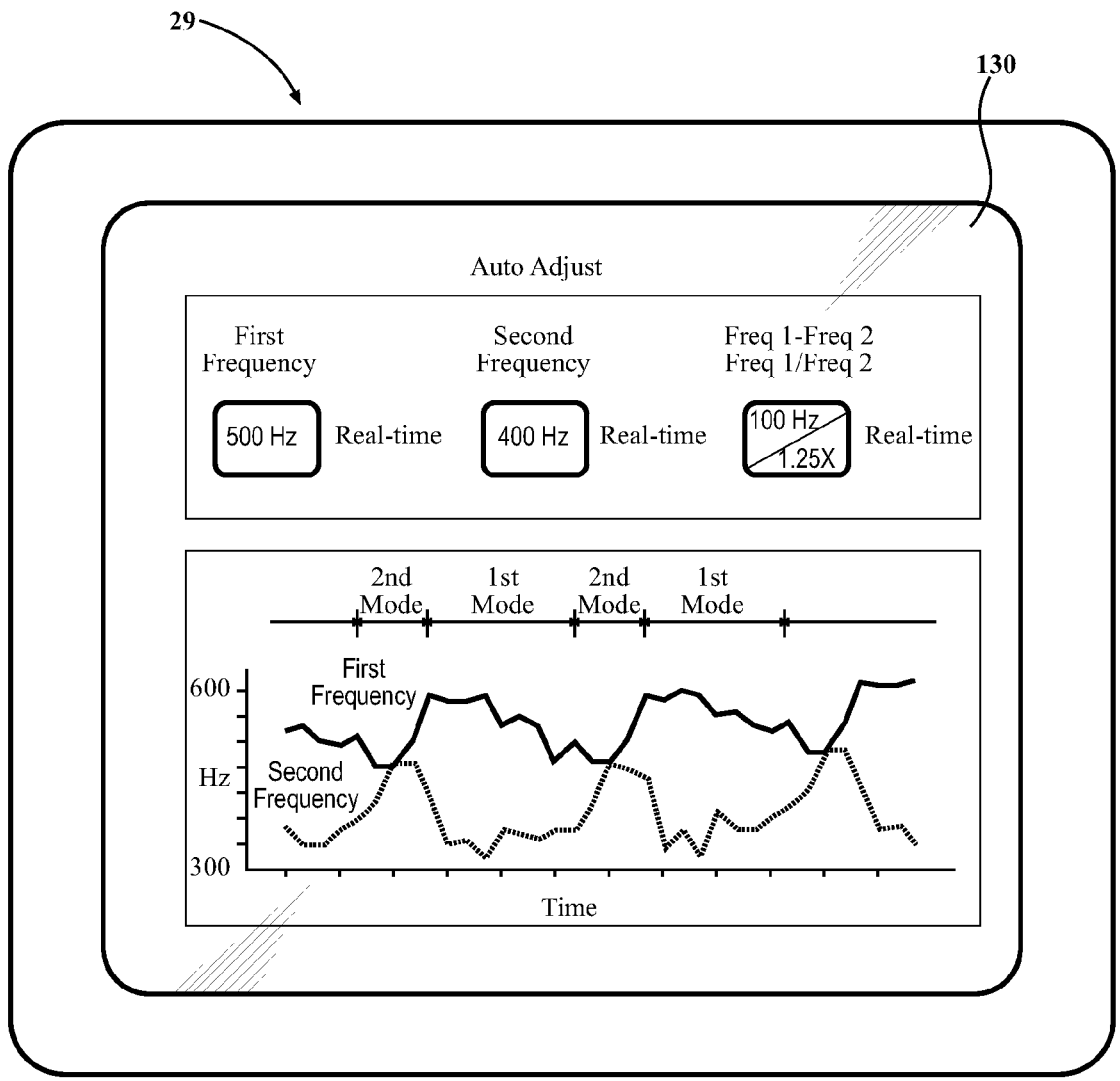
FIG. 6 is a perspective view of an interface according to one embodiment for allowing manual frequency adjustment and manual position control mode selection.

In one embodiment, as shown in FIG. 6, adjusting at least one of the first and second frequencies occurs autonomously. In one instance, the first or second frequency is increased or decreased autonomously. In another instance, the difference between the first and second frequencies is adjusted autonomously.

As shown in FIG. 6, the system may include a user interface 130 in communication with the frequency controller 120. In one embodiment, the user interface 130 is the navigation interface, including the first display 28 and/or second display 29. The user interface 130 communicates to the medical personnel information pertaining to the autonomous adjustment of the first and second frequencies. In one embodiment, the user interface 130 displays real-time autonomous adjustment of the first and second frequencies. The user interface 130 may display the numerical real-time frequencies as well as the real-time difference between the frequencies. In some instances, the user interface 130 may further display a magnitude of the difference between the first and second frequencies calculated by dividing the first frequency by the second frequency. For example, as shown in FIG. 6, the first frequency is 1.25× greater than the second frequency. Additionally, the user interface 130 may display graphical information, such as a chart, illustrating real-time autonomous adjustment of the first and second frequencies. The user interface 130 may provide any other suitable information for assisting the medical personnel. For instance, the user interface 130 may juxtapose the real-time difference between the first and second frequencies with the estimated or real-time positional accuracy and positional speed of the tool 22.

Autonomous adjustment may occur in response to any suitable event. In one embodiment, the transformation update frequency is autonomously changed based on feedback. For example, autonomous adjustment may occur when the system is engaged in an autonomous or semi-autonomous mode of operation, as described above. Additionally, autonomous adjustment may occur in response to a determined stability or instability of the system. In yet another example, autonomous adjustment occurs in response to determining the target area of interest. The first and second frequencies may be autonomously adjusted based on a size of the target area being treated. For instance, if the target area is sized such that the tool 22 cannot move greater than 10 mm in any direction, then the transformation update frequency may be autonomously lowered since the encoder-based data can be very precise when the tool 22 is operated in small areas. On the other hand, if the target area is sized such that the tool 22 can move greater than 100 mm in any direction, the transformation update frequency may autonomously set higher.

Furthermore, autonomous adjustment of the first and second frequencies may occur in response to switching between the first and second position control modes. Changes to the first or second frequency may be associated, for instance, when the robotic manipulator 56 is transitioning from a gross or bulk cutting operation, which requires less positional accuracy to a final or fine cutting operation, which requires greater positional accuracy. This could occur when a bulk cutting bur of tool 22 is replaced with a fine cutting bur. The burs may be automatically recognized by the manipulator controller 54 when inserted and thus switch the position control module between position control modes.

Similarly, the selection of the first or second position control modes may occur autonomously. Autonomous selection of the first or second position control modes may occur in response to any suitable event, including, but not limited to, those events described above in relation to autonomous adjustment of the first and second frequencies. Other situations may require automatically switching between position control modes for different reasons. Additionally, the user interface 130 may display any suitable information pertaining to autonomous selection of the first or second position control modes.

Figure 7:
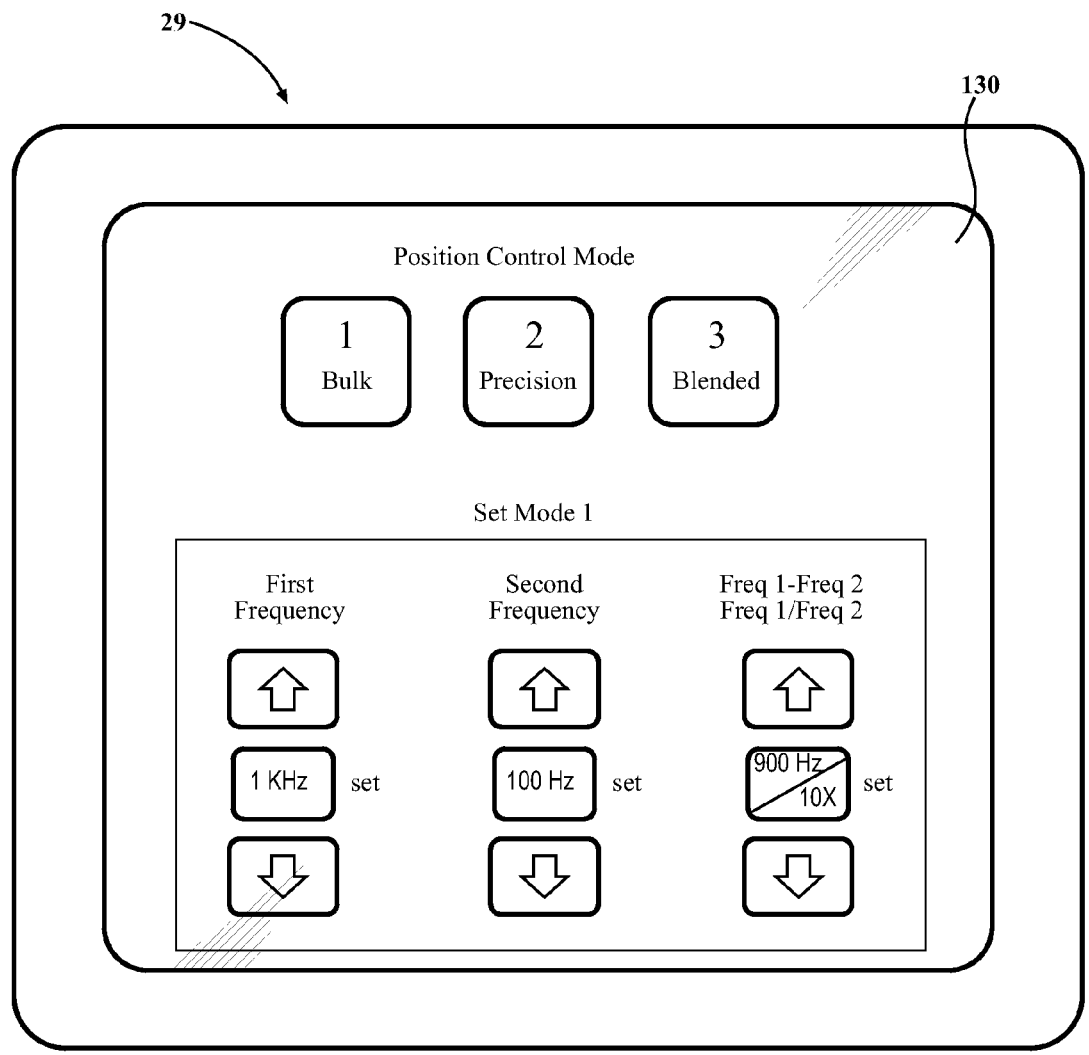
FIG. 7 is a perspective view of an interface according to another embodiment for displaying autonomous frequency adjustment and autonomous position control mode selection.

In another embodiment, as shown in FIG. 7, adjusting at least one of the first and second frequencies occurs manually. The user interface 130 enables the medical personnel to selectively adjust at least one of the first and second frequencies. For example, the user interface 130 may allow the medical personnel to selectively increase or decrease the first or second frequency for any given position control mode. The user interface 130 may also allow selective adjustment of the difference between the first and second frequency. The user interface 130 may allow such manual adjustment for any given position control mode. In one embodiment, manual adjustment of the first and second frequencies may occur in response to user inputted parameters. The system may include a position control module 109 that is a software module operated by the navigation computer 26 to change the first or second frequency based on desired parameters input into the guidance station 20. These parameters could include desired accuracy, precision, time of surgery, combinations thereof, and the like. Of course, manual adjustment of the first or second frequencies may occur in response to any other suitable event, including, but not limited to, those events described above in relation to autonomous adjustment of the first and second frequencies.

The first and second frequencies and/or the difference between the first and second frequencies can be set and stored in memory for each given position control mode. For example, in FIG. 7, a sample first position control mode (bulk) is selected with the first frequency set at 1 KHz and the second frequency set at 100 Hz. The set parameters may be stored in memory and loaded when this position control mode is selected at a later time.

Additionally, selection of the first and second position control modes may occur manually. The user interface 130 enables the medical personnel to manually select the first and second position control modes, or among a plurality of other position control modes or blend of modes. Manual selection of the first or second position control modes may occur in response to any suitable event, including, but not limited to, those events described above in relation to autonomous selection of the first and second position control modes.

Through manual adjustment of the first and second frequencies and/or manual selection of the first and second position control modes, the user interface 130 allows customized control over the positional accuracy and speed of the tool 22.

In some embodiments, adjusting the first and second frequencies occurs manually while selection of the first and second position control modes occurs autonomously. Alternatively, adjusting the first and second frequencies may occur autonomously while selection of the first and second position control modes occurs manually.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for interacting with an object, said system comprising:
   a robotic manipulator having a base and a plurality of linkages;
   a tool coupled to said robotic manipulator and movable relative to said base to interact with the object;
   a plurality of position sensors associated with said plurality of linkages for providing primary position information at a first frequency;
   a localizer for providing secondary position information at a second frequency;
   a position controller configured to position said tool with respect to the object in a first position control mode and a second position control mode based on said primary position information and said secondary position information; and
   a frequency controller configured to adjust at least one of said first and second frequencies in each of said first and second position control modes so that a difference between said first and second frequencies in said first position control mode is different than a difference between said first and second frequencies in said second position control mode.

2. The system as set forth in claim 1 wherein said primary position information includes encoder-based position commands for commanding movement of said tool in a manipulator coordinate system.

3. The system as set forth in claim 2 wherein said secondary position information includes navigation-based position and orientation data transformed from a localizer coordinate system to the said manipulator coordinate system.

4. The system as set forth in claim 1 wherein said difference between said first and second frequencies in said first position control mode is greater than said difference between said first and second frequencies in said second position control mode.

5. The system as set forth in claim 1 wherein said difference between said first and second frequencies in said first position control mode is non-zero.

6. The system as set forth in claim 1 wherein said first frequency is greater than said second frequency in said first position control mode.

7. The system as set forth in claim 1 wherein said difference between said first and second frequencies in said second position control mode is zero.

8. The system as set forth in claim 1 wherein said first frequency is substantially equal to said second frequency in said second position control mode.

9. The system as set forth in claim 1 wherein said second frequency is approximately $\frac{1}{10}$ or less of said first frequency in said first position control mode and said second frequency is equal to or greater than $\frac{1}{10}$ of said first frequency in said second position control mode.

10. The system as set forth in claim 1 wherein said difference between said first and second frequencies influences a positional speed of said tool.

11. The system as set forth in claim 10 wherein said positional speed of said tool in said first position control mode is greater than said positional speed of said tool in said second position control mode.

12. The system as set forth in claim 1 wherein said difference between said first and second frequencies influences a positional accuracy of said tool.

13. The system as set forth in claim 12 wherein said positional accuracy of said tool in said second position control mode is greater than said positional accuracy of said tool in said first position control mode.

14. The system as set forth in claim 1 further including an interface coupled to said frequency controller for enabling selective adjustment of at least one of said first and second frequencies.

15. The system as set forth in claim 1 further including an interface coupled to said frequency controller for enabling selection of said first and second position control modes.

16. The system as set forth in claim 1 wherein said plurality of position sensors include a plurality of position encoders.

17. A method for positioning a tool in a robotic system, the robotic system comprising a robotic manipulator having a base and a plurality of linkages with the tool coupled to the robotic manipulator and being moveable relative to the base to interact with an object, a plurality of position sensors associated with the plurality of linkages, a localizer for providing secondary position information, and one or more controllers, said method comprising:
    providing primary position information via the position sensors at a first frequency;
    providing secondary position information via the localizer at a second frequency;
    the one or more controller executing the steps of:
        moving the tool in a first position control mode and a second position control mode based on the primary position information and the secondary position information; and
        adjusting at least one of the first and second frequencies in each of the first and second position control modes so that a difference between the first and second frequencies in the first position control mode is different than a difference between the first and second frequencies in the second position control mode.

18. The method of claim 17 wherein providing primary position information includes generating position commands for commanding movement of the tool in a manipulator coordinate system at the first frequency.

19. The method claim 17 wherein providing secondary position information includes updating transformation of navigation-based position and orientation data from a localizer coordinate system to a manipulator coordinate system at the second frequency.

20. The method of claim 17 further including influencing a positional speed of the tool based on the difference between the first and second frequencies such that the positional speed in the first position control mode is greater than the positional speed in the second position control mode.

21. The method of claim 17 further including influencing a positional accuracy of the tool based on the difference between the first and second frequencies such that the positional accuracy in the second position control mode is greater than the positional accuracy in the first position control mode.

22. The method of claim 17 wherein adjusting at least one of the first and second frequencies occurs autonomously.

23. The method of claim 17 wherein adjusting at least one of the first and second frequencies occurs manually.

24. The method of claim 17 further including manually selecting at least one of the first and second position control modes.

25. The method of claim 17 further including autonomously selecting the first and second position control modes.

* * * * *